(12) United States Patent
Wild

(10) Patent No.: US 6,605,036 B1
(45) Date of Patent: Aug. 12, 2003

(54) SURGICAL INSTRUMENT ASSEMBLY FOR USE IN ENDOSCOPIC SURGERY

(76) Inventor: Andrew Michael Wild, P.O. Box 35, St. Neots, Huntingdon, Cambridgeshire PE19 3UY (GB)

(*) Notice: Subject to any disclaimer, the term of this patent is extended or adjusted under 35 U.S.C. 154(b) by 222 days.

(21) Appl. No.: 09/618,679

(22) Filed: Jul. 19, 2000

Related U.S. Application Data

(63) Continuation of application No. 09/188,445, filed on Nov. 9, 1998, now abandoned, which is a continuation of application No. PCT/GB97/01292, filed on May 12, 1997.

(30) Foreign Application Priority Data

May 10, 1996 (GB) .............................................. 9609750

(51) Int. Cl.[7] .............................................. A61B 1/012
(52) U.S. Cl. ........................ 600/131; 600/104; 600/114
(58) Field of Search .................... 600/104, 105, 600/106, 131, 114; 606/1, 205

(56) References Cited

U.S. PATENT DOCUMENTS

| | | | |
|---|---|---|---|
| 4,273,109 A | 6/1981 | Enderby | 128/6 |
| 4,319,563 A | 3/1982 | Kubota | 128/6 |
| 4,557,255 A * | 12/1985 | Goodman | 600/104 |
| 4,607,620 A | 8/1986 | Storz | 128/4 |
| 4,896,678 A | 1/1990 | Ogawa | 128/751 |
| 4,924,851 A * | 5/1990 | Ognier et al. | 600/106 |
| 5,088,819 A * | 2/1992 | Storz | 356/241.1 |
| 5,112,329 A | 5/1992 | Storz | 606/46 |
| 5,147,378 A | 9/1992 | Markham | 606/206 |
| 5,183,031 A * | 2/1993 | Rossoff | 600/120 |
| 5,222,973 A | 6/1993 | Sharpe et al. | 606/206 |
| 5,258,005 A | 11/1993 | Christian | 606/205 |
| 5,281,214 A | 1/1994 | Wilkins et al. | 606/15 |
| 5,368,605 A | 11/1994 | Miller, Jr. | 606/170 |
| 5,470,328 A | 11/1995 | Furnish et al. | 606/1 |
| 5,632,717 A * | 5/1997 | Yoon | 600/104 |
| 5,658,236 A * | 8/1997 | Sauer et al. | 600/105 |
| 5,766,169 A * | 6/1998 | Fritzsch et al. | 606/46 |
| 5,972,020 A * | 10/1999 | Carpentier et al. | 294/104 |
| 6,428,538 B1 * | 8/2002 | Blewett et al. | 606/46 |

FOREIGN PATENT DOCUMENTS

| | | |
|---|---|---|
| EP | 0 552 430 A1 | 7/1993 |
| EP | 0 610 099 A2 | 8/1994 |
| EP | 0 695 534 A2 | 2/1996 |
| GB | 2 004 794 A | 4/1979 |
| WO | WO 91/02493 | 3/1991 |
| WO | WO 92/19146 | 11/1992 |
| WO | WO 93/20759 | 10/1993 |
| WO | WO 94/10920 | 5/1994 |
| WO | WO 94/20025 | 9/1994 |
| WO | WO 95/05116 | 2/1995 |
| WO | WO 95/09566 | 4/1995 |
| WO | WO 96/24298 | 8/1996 |

* cited by examiner

*Primary Examiner*—John P. Leubecker
(74) *Attorney, Agent, or Firm*—Nixon Peabody LLP

(57) ABSTRACT

A surgical instrument assembly includes a surgical instrument having a proximal handle (16) for control by the surgeon, the handle being ergonomically configured and having surface depressions (17, 18, 19, 20) to accommodate thumb and finger tips. The handle extends no more than about 5 cm beyond the point of grip so that the surgeon can rotate his/her hand over the end of the handle in unrestricted movement while maintaining the grip between thumb and middle finger. Improvements in the support means for the endoscope telescope and instrument shaft, as well as in the lighting system of the assembly are also disclosed, together with improvements in the mechanisms for moving a distal end of the instrument in the operating zone within a patient.

16 Claims, 11 Drawing Sheets

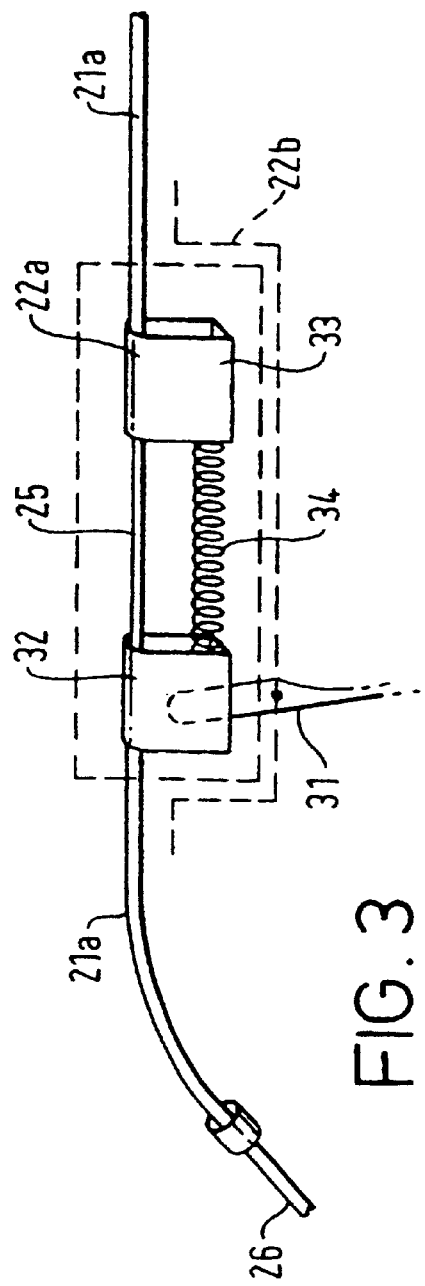
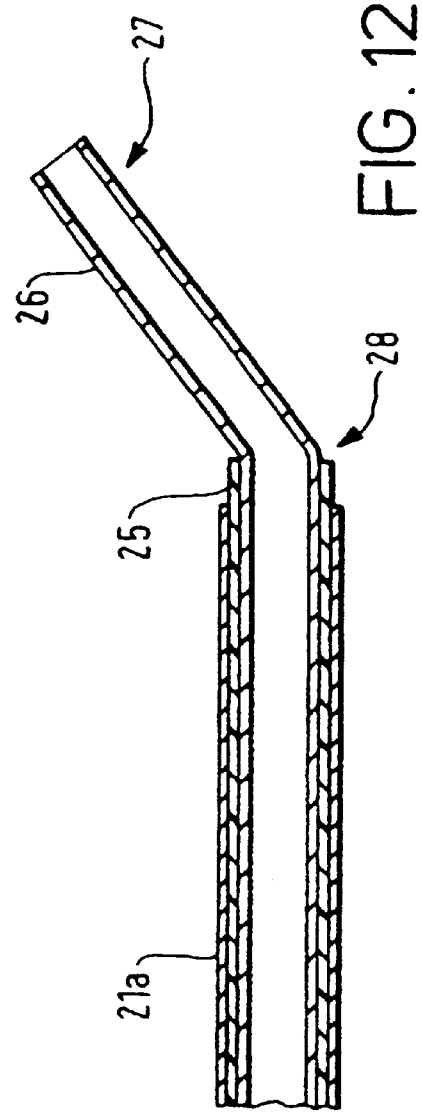

(a)         (b)

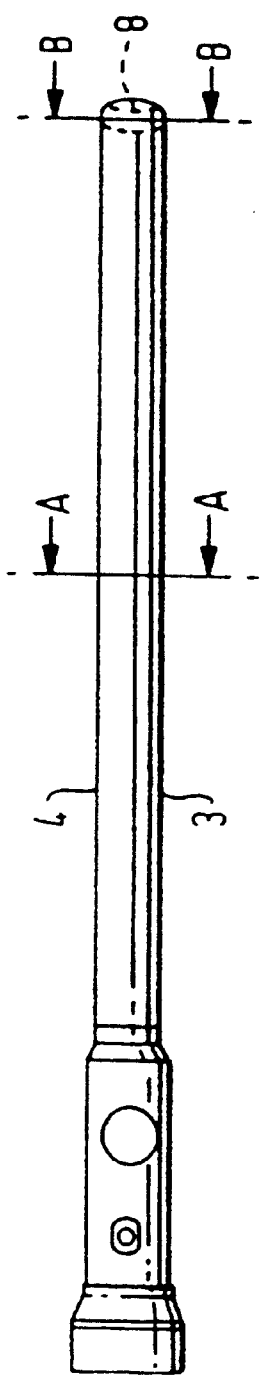
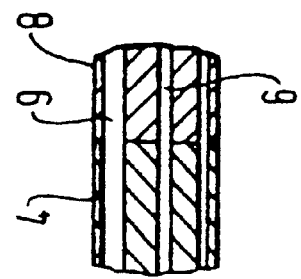
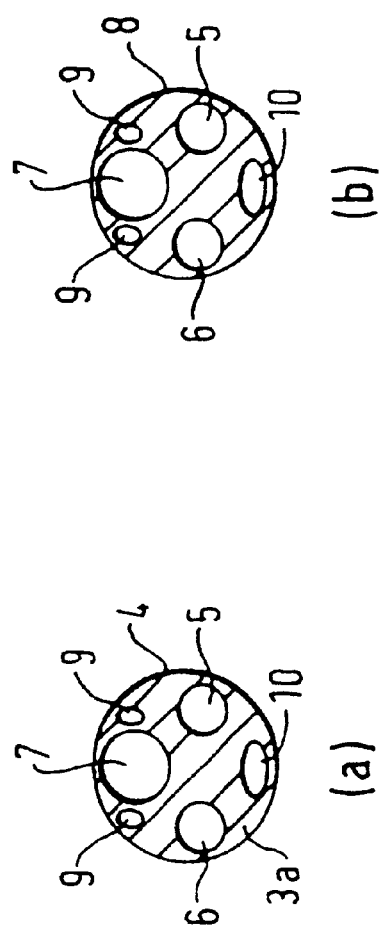
FIG. 16
FIG. 17
FIG. 18

SURGICAL INSTRUMENT ASSEMBLY FOR USE IN ENDOSCOPIC SURGERY

This application is a continuation of application U.S. Ser. No. 09/188,445 field Nov. 9, 1998, now abandoned, which is a continuation of PCT/GB97/01292, field May 12, 1997.

FIELD OF THE INVENTION

The present invention relates to a surgical instrument assembly for use in endoscopic surgery, particularly endoscopic neurosurgery.

BACKGROUND OF THE INVENTION

Surgical instrument assemblies for use with rigid or flexible endoscopes are well known in biopsy procedures and certain types of endosurgery. A telescope portion of the endoscope is generally housed within a sleeve which also houses the shaft of a single surgical instrument. The sleeve and surgical instrument each has a proximal end and a distal end. The distal end of the surgical instrument is an operative end having an operative function. The operative end of the surgical instrument protrudes from the distal sleeve end into a field of view of the endoscope, and is controllable from the proximal end by the surgeon. Such assemblies have been widely used in relatively simple procedures where lateral to and fro manipulation of the operative end of the surgical instrument within the field of view is not required.

Systems permitting manipulation of a flexible distal end portion of a surgical instrument (e.g. a catheter or flexible surgical tool) in one lateral to and fro direction within the field of view are also known. Thus, for example, U.S. Pat. No. 2,038,394 (Wappler) describes a catheterising cystoscope, having the facility to deflect the distal end of a catheter inserted into a body cavity, within a field of view of an endoscope. British Patent Application No. 2004749 describes a modification of such a system, in which a proximal operating lever is provided to control a deflector at the distal end, which lever may be manipulated by the fingers of the hand used for holding the assembly. Furthermore, the operating mechanism of the lever is spring-loaded to cause return of the lever (and return of the deflector) when the finger pressure is released. In this way, the lateral to and fro manipulation of the flexible end portion of the surgical instrument is accomplished by the surgeon using one finger of one hand to manipulate the operating lever. The surgeon can thus use the same hand for adjusting the angular position of the deflector, while using the other hand to advance, twist or withdraw the instrument.

Such unifunctional instrument assemblies have found use in neurosurgery and other relatively complex procedures, including aspiration of intracerebral hematomas, drainage of chronic subdural hematomas, the fenestration of arachnoid and other cysts, third ventriculostomy, choroid plexus fulguration and spinal disc exenteration. In some of these systems a second or subsequent surgical instrument may be introduced down a parallel sleeve, but the systems lack the means for concerted interaction between surgical instruments.

Neuroendoscopic surgery shows a wealth of potential as a neurosurgical technique, which has hitherto been substantially unrealised due to a lack of appropriate surgical equipment. Unlike other current trends in computer-assisted point targeting systems, neuroendoscopy is primarily an optical system in the tradition of macro- and microsurgery. The great hope for endoscopy is its ability to provide for a minimal approach. Parallel function, with instrument systems which operate independently of the endoscopic position, can allow for a confined approach, with a reduction in unnecessary lateral dissection and retraction. This is enhanced by the greater ease with which paraxial areas can be seen, and with flexible endoscope systems more peripheral areas could also be visualized from within the same minimal approach. Endoscopy also enables stability in the operating system and instruments, in contradistinction to microsurgery, where the stability of the instruments is directly dependent upon the surgeon and his or her ability to operate in an awkward postural position, which in turn is subservient to the optimal position of the microscope. With endoscopy the use of television monitors from which to operate can give the surgeon enormous postural freedom and freedom of movement, with the instruments held at a convenient distance from the body. With the added stability imparted to the instruments by the endoscopic system, it is likely that neuroendoscopy is easier to master than microsurgery.

A particular advantage of endoscopy is that it is depth independent. With the optical viewing point at, or around, the tissue-instrument interface regardless of the depth, this means that the same viewing quality is maintained throughout. Endoscopy can provide a really excellent view of the tissue and instruments; if the optical telescope function is made independent of the parent endoscope as will be discussed in greater detail below, a variety of viewing perspectives could be easily attained, without altering the overall intracranial position of the parent endoscope.

In International (PCT) Patent Application No. WO 92/19146 there is described (FIGS. 10 and 11) a laser instrument for use in neuroendoscopic and similar delicate procedures, having an ergonomic handle to provide specific control. The instrument comprises a thin rigid hollow shaft carrying an internal laser fibre and having a distal end provided with a deflector for the fibre and a proximal end to which is pivotally attached the ergonomic control handle. The handle is hollow and internally carries the laser fibre, apart from one portion of the fibre which lies exposed against the outside of the handle. Fine control of advancement/retraction of the laser fibre is provided by simple index finger pressure by the surgeon on the exposed portion of the fibre to press it against the handle. The handle is connected to the deflector via a push-pull wire pair passing through the hollow shaft and arranged so that pivotal movement of the handle causes the deflector to move to deflect the operative end of the laser fibre. The instrument is mounted with an endoscope telescope in an instrument assembly during use. Generally similar instruments are also described, in which the distal end has a mechanically operable function (e.g. a bipolar diathermy tool, a rongeurs tool or a forceps tool) and the handle is provided with a rocker mechanism operated by the surgeon's index and middle fingers to control the operation of the instruments.

The ergonomic handle of the instruments described in WO 92/19146 is an elongate handle of a "pencil grip" type. It suffers from three prime disadvantages. Firstly, the use of the rocker mechanism for controlling mechanically operable distal end parts makes it difficult for the surgeon to grip the handle securely without fear of inadvertently moving the distal end of the instrument. Secondly, the handle of the laser instrument, which in contrast to the other instruments described can be securely gripped between the surgeon's thumb and middle finger, is attached to laser generating apparatus and the surgeon cannot move his or her hand around the end of the handle while maintaining a secure grip between the thumb and middle finger. Thirdly, the pivoting of the handle to control the instrument deflection function requires an inconvenient wrist movement by the surgeon.

SUMMARY OF THE INVENTION

It is an object of the present invention to provide an improved or at least alternative surgical instrument assembly for use in endoscopic surgery, particularly endoscopic neurosurgery.

According to a first aspect of the present invention, there is provided a surgical instrument assembly for use in endoscopic surgery, particularly endoscopic neurosurgery, the assembly comprising:

(a) a surgical instrument having proximal manually operable instrument control means and distal operative means coupled thereto, the operative and control means being spaced mutually apart by a shaft, and a handle being provided in general proximity to the control means whereby a surgeon can hold the instrument;

(b) optical means (more particularly an endoscope telescope and lighting system) for viewing a distal end of the instrument in an operating zone within a patient; and (c) support means for retaining the instrument and optical viewing means in use so as to present the distal end of the instrument for viewing in the operating zone within the patient and to present the control means externally of the patient for manipulation by the surgeon;

characterised in that: the handle is ergonomically configured as a generally elongate handle provided with surface depressions arranged to accommodate at least a thumb tip and middle finger tip of the surgeon whereby the surgeon can grip fast the handle substantially directly between thumb and middle finger; and the handle extends no more than about 5 cm beyond the point of grip and the instrument is adapted to permit the surgeon to rotate his/her hand around the handle in unrestricted movement while maintaining the grip between thumb and middle finger.

The handle is preferably mounted fast to the instrument, i.e. without any pivotal movement between handle and instrument, and most preferably extends at right angles to the longitudinal direction of the shaft. The handle and control means are conveniently releasably mounted to the shaft as a removable, reusable, unit as will be discussed in greater detail below. The unit is most preferably sterilisable (e.g. autoclavable) for reuse and constructed from lightweight materials to minimise hand fatigue and maximise responsiveness. Metals such as aluminium or titanium are mentioned as particularly suitable. Synthetic materials such as lightweight resins may also be used.

The handle may if desired be hollow, to minimise its weight. In this case, it is preferred that the handle is formed as a releasable pair of handle halves, to allow all interior surfaces to be effectively sterilised for reuse.

The surface depressions for the surgeon's thumb tip and middle finger are suitably provided at approximately the midpoint along the length of the handle. Further surface depressions are preferably provided in the handle to accommodate the surgeon's index and/or fourth finger tips. Each depression is preferably approximately 2 to 8 mm, e.g. about 5 mm, deep and approximately 10 to 30 mm, e.g. about 15 to 20 mm, long.

The instrument control means are provided in general proximity to the handle. More particularly, it is preferred that the instrument control means are arranged to be operable by the surgeon's index and/or fourth finger without releasing the grip on the handle between the thumb and middle finger. For this purpose, the instrument control means may suitably comprise one or more triggers, levers, wheels or similar actuating members operatively coupled to the distal operative means of the instrument. The actuating member(s) is/are preferably spaced from, but close to, the surface depression provided in the handle for the surgeon's index and/or fourth finger tip, whereby the surgeon can simply extend his or her index or fourth finger away from the handle to operate the desired actuating member, and subsequently return the finger to rest on the handle.

The number of actuating members is determined by the functionality of the instrument. The instruments of prime utility in delicate endoscopic surgical procedures all have at least a distal deflection function, whereby the distal end of the instrument can be moved laterally to and fro within the field of view. In such instruments the primary operative means is the distal end deflection system. In addition, instruments may have secondary and further functions, each of which will have their own associated distal operative means, each of which in turn may either be coupled to their own proximal manually operable instrument control means or to alternative instrument control means such as pedal or other remote controls.

Thus, for example, suction instruments, dissection forceps, laser fibre applicators, non-crushing grasping forceps, biopsy rongeurs, scissors, arachnoid dissectors and bipolar diathermy instruments may all be used; the primary operative means is a distal end deflector system, with in some cases secondary distal operative means actuating jaws, blades, cusps etc. Possible additional functionality may include heating (diathermy).

The handle preferably performs no direct instrument control function itself; however, in an alternative embodiment an adjacent trigger or lever instrument actuating member can be conformed so that, when brought fast to the handle on full actuation of the instrument function concerned, that actuating member and the handle together constitute a handle for the instrument according to the first aspect of the invention.

Operative coupling of the proximal manually operable instrument control means to the distal operative means of the instrument may be accomplished via a push-pull mechanical linkage of the type generally described in PCT Patent Application No. Wo 92/19146 (the disclosure of which is incorporated herein by reference). However, such coupling imposes a minimum size on the shaft and distal end of the instrument, which is undesirably large for neurosurgery, where instruments of diameter of approximately 2 mm are ideally required. Accordingly, it is preferred that the operative coupling is effected by means of longitudinally slidable parts associated with or comprising the shaft of the instrument and bearing against elastic or resilient operative portions at the distal end of the shaft. Alternatively, but less preferably, hydraulic and/or pneumatic coupling may be used.

The use of longitudinally slidable parts associated with or comprising the shaft of a surgical instrument, to effect operative coupling of proximal manually operable instrument control means thereof and distal operative means thereof, is new per se, and constitutes a second aspect of the present invention, irrespective of whether or not such instruments are used in a surgical instrument assembly according to the first aspect of the invention.

In more detail, the preferred operative coupling system in the case of a unifunctional instrument for which only a primary distal deflection function is required under the surgeon's manual control comprises a generally firm but pliant outer tube constituting an outer sheath part of the shaft of the instrument, an operative inner part of the shaft of the instrument lying within the tube and the distal end of the operative inner part of the instrument projecting from a distal end of the outer tube and angulated away from the axis of the instrument at or near the point of exit from the distal end of the tube. The instrument control means are preferably arranged so that on movement of the actuating member by the surgeon's finger a longitudinal relative sliding movement is mechanically imparted between the operative inner part of the instrument and the outer tube causing the distal end of the tube to overlie the angulated portion, which thereby causes the distal end of the instrument to straighten. The deflection is preferably induced against the restoring force of resilient means (e.g. a spring) associated with the actuating member, so that the instrument returns to its resting condition on release of the surgeon's finger pressure.

The operative inner part of the shaft of the instrument may, for example, be a suction tube or a laser fibre. The operative inner part of the shaft of the instrument is preferably anchored to the handle portion of the instrument, with the outer sheath part of the shaft movable in the desired relative sliding motion.

In the case of a multifunctional instrument, the single tube is replaced by a coaxial pair of slidable tubes one housed within the other. The distal end of the inner tube projects from the distal end of the outer tube and is angulated away from the axis of the instrument analogously to the instrument lying within the inner tube. As before, the operative inner part of the shaft of the instrument is preferably anchored to the handle portion of the instrument, with the pair of tubes being movable in the desired relative sliding motion. The distal deflection function is analogous to that described for a unifunctional instrument, save that the inner tube is also straightened by the relative movement of the inner and outer tubes. The operative inner part of the shaft of the instrument, lying within the tube pair, suitably comprises control parts for secondary operative means projecting from the distal end of the inner tube. Such control parts may, for example, be anchoring limbs for operative distal jaws, blades or cusps, which anchor the operative means to the handle to permit said relative sliding movement of the overlying tube parts.

The secondary function, which may for example be closing/opening of the secondary operative means such as jaws, blades or cusps projecting from the distal end of the inner tube, is achieved by arranging the instrument control means so that, on movement of the relevant actuating member by the surgeon's finger a longitudinal relative sliding movement is mechanically imparted between the operative inner part of the shaft of the instrument and the inner tube (but not between the operative inner part of the shaft of the instrument and the outer tube).

By arranging the operative inner part of the shaft of the instrument and the inner tube so that the inner tube constitutes a yoke overlying secondary operative means control parts of the instrument which are arranged to move in response to sliding movement of the yoke and thereby to actuate the secondary operative means of the instrument, the said longitudinal relative sliding movement between the control parts and the inner tube causes the distal secondary operative means of the instrument to be actuated. In a manner analogous to the unifunctional system, the relevant actuating member for the secondary function is associated with resilient means (e.g. a spring) which provides a restoring force returning the instrument to its resting condition on release of the surgeon's finger pressure. Moreover, by constructing the secondary operative means control parts of the instrument from a resilient material such as elastic metal, and arranging that the yoke-induced movement of those parts is against the resilient restoring force the control parts will similarly return to their resting condition, causing the secondary operative means of the instrument to correspondingly return to their resting condition on release of the surgeon's finger pressure.

The actuating systems described above enable a variety of surgical instruments to be constructed for use in endoscopic surgery, at far smaller diameters than conventional lever (mechanical) based mechanisms currently permit.

The optical viewing Means is particularly an endoscopic telescope, which may be a flexible or rigid optical system of conventional construction. The surgeon may wish to use one of a range of telescopes depending on the requirements of the surgical procedure. For example, it can be useful sometimes to use a flexible mini-endoscope, or at other times rigid telescopes having different angled field collecting lenses. The optical viewing means will be used in conjunction with lighting systems of generally conventional construction (e.g. fibre optic illumination of the field of view). However, it is preferred that, in the instrument assembly of the present invention, the lighting system is not integral with the optical viewing means, and that the two are movable independently of each other. In this way, an endoscope telescope, for example, can be advanced/retracted or otherwise moved independently of a fibre optic bundle and in conjunction and synchrony with the instruments, as will be discussed in greater detail below.

A stereoscopic endoscopic telescope should preferably be used, although this is not essential. Such a system requires a double viewing system equivalent to two parallel telescopes, and the resultant increased size may be inconvenient in some surgical procedures.

The telescope is suitably linked in conventional manner to a closed-circuit video camera system, which is preferably integral with the assembly.

Alternatively, a flexible endoscope such as a flexible mini-endoscope can be used as the main telescopic system. Steerable flexible endoscopes are preferred, but in this event means must be provided for locking the endoscopic telescope in position. Such a steerable endoscope typically incorporates three push-pull wires attached to a short distal rigid section containing the field collecting lens system, the wires being used to deflect the rigid section in any desired direction.

Forward oblique endoscope telescopes are generally preferred, having a maximum of about 30° field collecting lens to reduce distortion during close-up viewing.

The telescope may suitably be connected to a closed-circuit video camera for ease of visualisation. It is preferred that a novel design of telescope lens is employed with the assembly of the present invention, as will be described in greater detail below.

The support means for retaining the instrument and optical viewing means in use must be capable of securely anchoring any optical telescope as any accidental movement of such a heavy piece of equipment in a neurosurgical operating zone can be fatal to the patient. This risk is especially acute when a closed-circuit video camera or other viewing or lighting equipment is mounted to the telescope. The anchoring will preferably be releasable, as one of the advantages of the assembly of the invention will be that the optical viewing system can be rotated and adjusted to alter the surgeon's field of view. The support system is of generally conventional construction known for rigid endoscopes and is preferably securely mounted to an operating table so that accidental movement with respect to the patient is impossible.

Most preferably, the support means comprises a rigid shaft having a plurality of parallel through channels extending along its length. A large slip-ring arrangement will suitably be provided in conventional manner, linked to a non-damaging (e.g. rubber) wheel projecting into the through channel for the telescope, to allow for the advance/retraction mechanism for the telescope. Rotation of the slip-ring by the surgeon's finger will cause slow advancement/retraction of the telescope via the rotation of the rubber wheel against the telescope.

In use the shaft extends into the operating zone and is securely anchored at the proximal end, typically via an easy-release fixation system of conventional arm construction used for endoscopes. The fixation system is attached to a detachable side handle provided on the shaft, which handle in turn is used for convenient positioning of both shaft and fixation system. When used properly these systems provide a stable operating platform from which to manipulate the instrumentation. The fixation system is preferably used to anchor the endoscope to the operating table or other support.

The lighting system is preferably a fibre optic bundle packed into all available space between the various channels of the shaft of the support means.

Fixation may also be effected via a stereotactic frame. Stereotaxy limits movement, but facilitates anatomical accuracy in applicable situations and is therefore preferred by some surgeons.

The fixation system should be distally attached to the operating table. It may alternatively be anchored to the skull in adults, but this alternative has been found to be less satisfactory, especially with the additional weight of a CCD camera. Free-standing systems are able to support this weight, but unless heavy and stable, are potentially lethal if knocked. Skull based fixation systems cannot be used in children, and are not practical for supporting weight. Table mounted systems are therefore the most satisfactory.

In use, the shaft of the support means preferably lies horizontal. The shaft should have an outer diameter of no more than about 6 mm. The optical channel, for housing the endoscopic telescope, suitably occupies the upper position in the shaft. The one or more working channels for housing the instrument(s) are suitably beneath the optical channel. It is preferred that two working channels are present, suitably of a design generally compatible with all instruments, so that the surgeon can operate bimanually with two instruments simultaneously.

Beneath the level of the working channels there is provided a passive fluid escape channel to allow drainage of fluid and debris from out of the operating zone. The passive fluid escape channel is connected proximally to a drainage tube providing gravity drainage and collection of all fluids.

Two small further irrigation channels are suitably further provided in the shaft of the support means, preferably either side of the optical channel, to enable a continuous flow of clear fluid across the field-collecting lens of the telescope, to remove debris from the field of view. Conventional control and fail-safe mechanisms are also provided to ensure that when irrigation fluid is used the intracranial pressure does not rise unduly. Neuroendoscopy requires constant irrigation and this is particularly crucial in the presence of bleeding or debris. A pressure and volume monitoring system of conventional construction is preferred for this purpose. The hydrostatic pressure of the irrigation fluid should be the minimum pressure under which passive fluid escape will still be satisfactorily accomplished via the passive fluid escape channel. The hydrostatic pressure should suitably be the lesser of 15 cm ($H_2O$) or L cm($H_2O$) (where L is the length of the shaft of the support means).

The channels will carry no teats, taps or stops, as these are inappropriate in neurosurgical systems where any tendency to build up intracranial fluid pressure must be avoided It is also desirable to avoid the necessity of direct transcerebral routes wherever possible and to adopt subarachnoid cisternal approaches to lesions within the head. This requires the use of compliant, responsive instrument systems, which can easily be manipulated at a distance from the immediate position of the parent endoscope.

The support means provides stability to the instrument system. The instrument shaft can thus be stabilized within the fixed working channel, so facilitating precise and delicate movement of the instrument working tip. This is readily achieved within a rigid endoscopic system. With flexible systems the proximal end of the flexible endoscope should also be stabilised via a fixation system, and the distal end easily "locked" in position to increase stability and facilitate bimanual instrument function. By using CCD cameras and operating from high-definition monitors, the surgeon does not have to adopt awkward operating postures of body or hands as one sees in microneurosurgery. This renders endosurgery easier to perform than microsurgery.

The provision of a lighting system (e.g. fibre optic bundle) as mentioned above, which is of fixed location relative to the support means and does not move with the endoscope telescope, provides substantial advantages to endoscopic surgical instruments in general, irrespective of whether or not they are present in an instrument assembly according to the present invention.

According to a further aspect of the present invention, therefore, there is provided a surgical instrument assembly for use in endoscopic surgery, particularly endoscopic neurosurgery, the assembly comprising:

(a) a surgical instrument having proximal manually operable instrument control means and distal operative means coupled thereto, the operative and control means being spaced mutually apart by a shaft, and a handle in general proximity to the control means whereby a surgeon can hold the instrument;

(b) optical means comprising an endoscope telescope and lighting system, for viewing a distal end of the instrument in an operating zone within a patient; and (c) support means for retaining the instrument and optical viewing means in use so as to present the distal end of the instrument for viewing in the operating zone within the patient and to present the control means externally of the patient for manipulation by the surgeon;

characterised in that: the lighting system is independent of the endoscope telescope and is of fixed location relative to the support means to illuminate a predetermined region of the operating zone relative to the support means;

the instrument shaft is retained by the support means in an orientation generally parallel to, but offset from, the endoscope telescope; and the endoscope telescope is movable in conjunction with the surgical instrument relative to the support means and lighting system.

The parts (a), (b) and (c) are preferably as described above in relation to the first aspect of the invention.

The lighting system is preferably generally concentric with the support means, for maximum illumination of the central operating zone.

By offsetting the axes of the instrument and the telescope a side view of the distal end of the instrument can advantageously be gained in the operating zone within the patient.

The above arrangement allows the telescope to be adjusted independently of the position of the support means and in conjunction with the instrument (s). The distal end of the telescope can therefore be maintained generally at an optimum separation from the distal operative means of the instrument(s), having regard to the image distortion found particularly with close or distant spacing of objects from the distal end of the telescope. The support means can then be fixed at a single advantageous position relative to the operating zone and not moved, while both the instrument(s) and telescope can be moved in concert. The telescope can be retracted into the support means and the exact entry point of the instrument(s) into the operating zone seen and controlled towards their target area(s).

During surgery the surgeon should be seated comfortably, with the support means of the instrument assembly of the present invention positioned horizontally. The instruments are introduced beneath the level of the optical telescope system (rigid lens or flexible system) and thereby enter the surgical field under direct vision for maximal safety. Thereafter manipulation of the instruments occurs in three planes, rotation around their long axis, advance/withdrawal into and out of the surgical field, and lateral movement distally by means of controlled deflection within the surgical field. Advance and withdrawal is simply effected, with rotation controlled by the novel instrument handles as defined. These should be set at 90° to the main shaft and allow 180° of rotation through the hand, when principally held between the thumb and third finger. This should be capable of being effected without ever needing to release the principal grip on the instruments. Primary and secondary function is preferably effected via a spring-trigger or analogous action, using the index finger, or alternatively the fourth finger depending on the disposition of the hand.

Furthermore, the optical viewing system can also be moved during the surgical procedure. Thus, the surgeon can move from an overview (for monitoring the status of neighbouring areas, e.g. any bleeding or inadvertent damage, and equally for orientation of the surgeon's position and progress along a particular approach) to a close-up view of a target area during an operation. In neuroendoscopy it is important to be able to perform this change without altering the position of the support shaft. Independent synchronized function allows the instruments to be followed throughout their trajectory without altering the position of the support shaft, and therefore minimizing damage to adjacent structures.

A particular difficulty with known endoscopic systems lies in the fact that the fibre optic bundles often become fouled with debris, brain tissue or blood, which reduces visibility and is difficult to correct without withdrawing the endoscope for cleaning, before re-introduction and commensurate increase in tissue trauma. Furthermore, light from such optical bundles is poorly focused within the operating zone. Delicate endbscopic surgical procedures require high quality lighting and optimal visibility at all times which known systems cannot adequately provide.

According to a further aspect of the present invention, therefore, there is provided a fibre optic light guide for illuminating an operating zone for endoscopic surgery (particularly endoscopic neurosurgery) within a patient, the light guide comprising elongate light-conveying optical fibres or fibre bundles having a distal end for illuminating the operating zone and contiguous at their distal end with a distinct smooth protective and physiologically benign, transparent, refractive lens providing a convex end surface (e.g. of glass or other suitably transparent refractive material) whereby the conveyed light is focused onto the operating zone and the optic fibres are not injured or fouled by tissue (especially brain tissue, debris or blood). Optimal visibility can thus be readily maintained under normal conditions.

The novel light guide is preferably used as the lighting system in the various aspects of the invention previously described. Where this lighting system is of fixed location relative to the support means of a surgical instrument assembly, the fibres or fibre bundles preferably lie within the support means so that the distal end of the fibres or fibre bundles corresponds to the distal end of the support means and the convex end surface of the lens overlying the fibres or fibre bundles is preferably at least partially, preferably substantially completely, contained within the diameter of the support means. In this way the lens width and its focusing effect are maximised while still keeping the light guide within the overall dimensions of the support means.

Where the support means takes the form of a shaft carrying a plurality of through-channels, corresponding channels are provided through the portion of the light guide which overlies the distal end of the shaft. Removable channel occluders are preferably also used to temporarily close the channels and reconstitute a perfect curved surface for the convex end surface during introduction of the assembly into the patient, to prevent tissue or fluids from fouling the channels.

DESCRIPTION OF THE DRAWINGS

For ease of understanding the present invention, embodiments will now be described, without limitation and purely by way of example, with reference to the accompanying drawings, in which:

FIG. 3 shows a schematic view of the internal mechanism of the handle portion of the surgical instrument of FIG. 2;

FIG. 12 shows a longitudinal sectional view of the distal end portion of the suction instrument of FIGS. 2 and 3;

FIG. 15 shows a longitudinal sectional view of the distal end portion of the forceps instrument of FIGS. 8 and 9;

FIG. 16 shows a simplified side elevational view of the assembly of FIG. 1;

FIG. 17 shows a transverse section view of the shaft of the assembly of FIG. 16 along the lines (a) A—A and (b) B—B; and FIG. 18 shows in longitudinal section an enlarged view of the distal end portion of the assembly of FIG. 16.

DETAILED DESCRIPTION OF THE INVENTION

Figure 1:
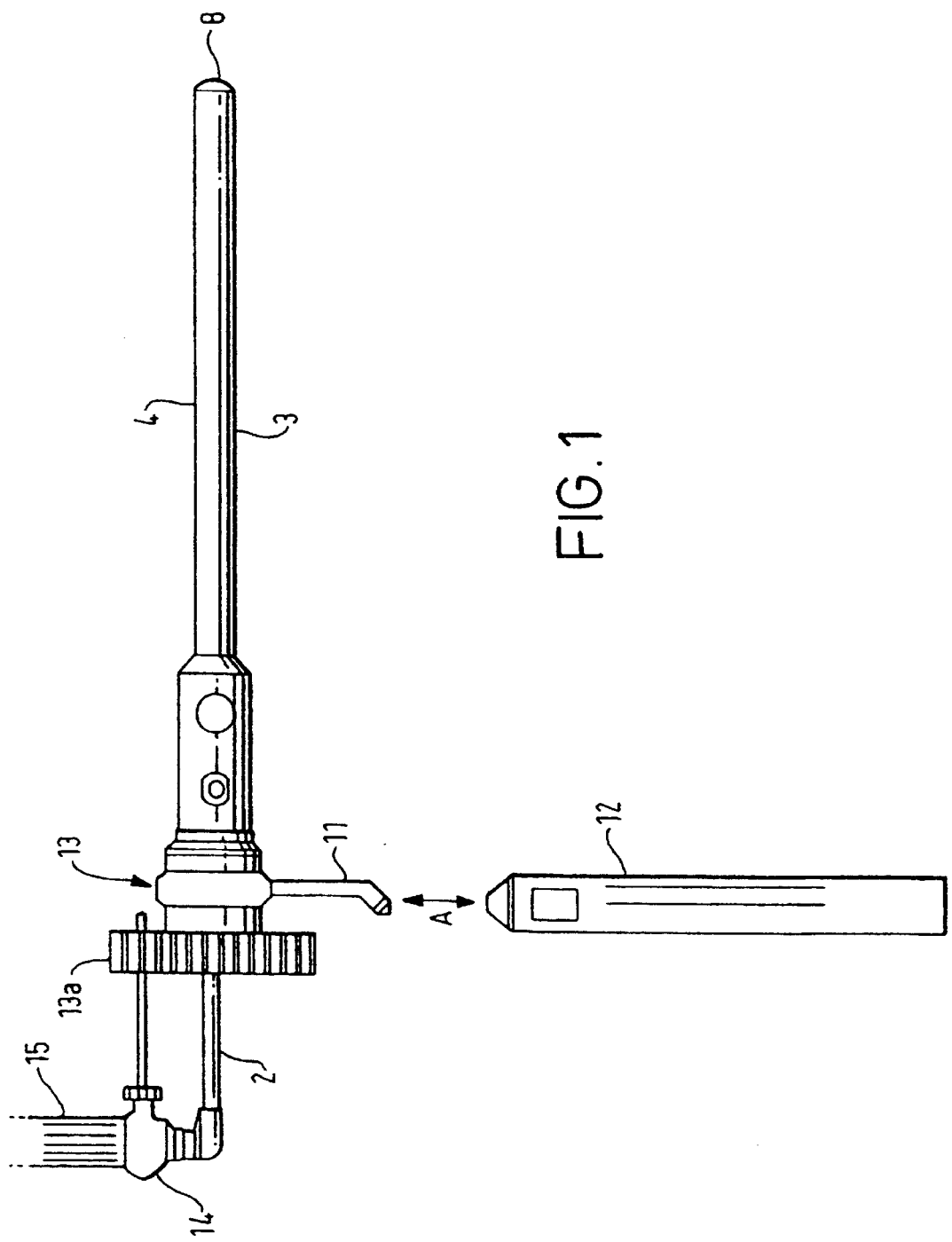
FIG. 1 shows a simplified side elevation view of a surgical instrument assembly for use in endoscopic surgery, particularly endoscopic neurosurgery.

Referring to the FIGS., in which like parts are designated alike, a surgical instrument assembly ("endoscope") for use in endoscopic surgery, particularly endoscopic neurosurgery, comprises a surgical instrument 1, an optical telescope 2 and fibre optic lighting system 3, and support means in the form of an outer shaft 4 provided with channels 5,6,7 for retaining respectively the instrument, an optional second instrument, and the telescope in use.

The telescope 2 is interchangeable in its channel 7 (the so-called "optical channel") with a range of alternative telescopes (not shown) selected from generally available endoscope telescope systems (e.g. rigid or flexible, stereoscopic or monoscopic, narrow or wide angle etc). A stereoscopic telescope system is generally preferred. The fibre optic lighting system 3 is integral with the endoscope shaft 4, in conventional manner for optical endoscopes, but is further provided with a novel distal lens system 8, extending across the distal end of the shaft, as will be described in greater detail below (see FIGS. 16 to 18).

The two instrument channels 5,6 are the so-called "working channels" for bimanual surgical function. The endoscope shaft 4 is additionally provided with irrigation 9 and passive fluid escape 10 channels, a detachable ergometric handle 11 and fixation system 12 (the handle 11 and fixation system 12 being interconnectable in conventional manner as indicated by double-headed arrow A in FIG. 1), and control mechanisms 13 for rotation, advance and withdrawal of the optical telescope 2 in relation to the instruments or main shaft 4 of the endoscope. The control mechanisms include a large slip-ring 13a, linked to an internal rubber wheel (not shown) bearing against the telescope within the optical channel 7, whereby the telescope 2 can be slowly advanced and retracted within the channel by turning of the slip-ring by the surgeon's finger. Parts 11,12, 13 and 13a are of conventional construction, and will be familiar to one of ordinary skill in this art.

A rigid telescope 2 is inserted through the optical channel 7 in the endoscope shaft 4, which may alternatively receive a small steerable flexible endoscope with laser fibre (not shown). The telescope functions to provide an optimal view within the surgical field of the distal ends of the instruments along their entire working trajectories. The control mechanisms 13 allow for rotation, advance and withdrawal of the optical telescope 2 in relation to the instruments or the endoscope shaft 4. This controlled independent optical function allows movement, either in concert with the instruments, or the ability to provide a range of view within the operative field, from a proximal overview of the anatomical position up to a distal close-up view of the instrument-tissue working interface. This is effected without altering the position of the main shaft of the parent endoscope.

The two working channels 5,6 lie below the level of the optical channel 7 and beneath them lies the passive escape fluid channel 10. Either side of the optical channel are the two small irrigation channels 9, providing clear fluid across the objective lens. This arrangement provides for a directional flow of clear fluid across the field collecting lens and down around the instruments, with escape of fluid and debris from underneath the working-viewing plane. Unlike cystoscopic based systems there are no teats or taps to any of the channels, so preventing fluid accumulation. All intervening space within the endoscope shaft is filled with the integral fibre-optic lighting system 3.

The handle 11 of the shaft can rotate about the long axis of the endoscope and provides a convenient advantage when introducing or guiding the position of the endoscope, as well as a point of attachment for the conventional fixation system 12. This system 12 provides firm support, which is also manoeuvrable when required. In this way the whole system provides stability to the instruments and optics, as a stable operating platform from which to manipulate the instruments in an unhindered manner. The endoscope and instruments may be manufactured to any length, but are preferably made to suit both 'freehand' and stereotactic applications.

The telescope 2 may be flexible or rigid and ideally both modes are used in combination, to provide the surgeon with the advantages of each. The assembly of the invention is designed to enable a readily interchangeable system of optics and instrumentation.

Referring now particularly to FIGS. 1, 16, 17 and 18, a a rigid endoscopic system is shown, having the outer shaft 4, no larger than about 6 mm diameter. The overall size is dependent upon the diameter of the optical telescope used, since the instrumentation (to be described in greater detail below) has an established minimal diameter of about 2 mm. The optical telescope 2 should be removable from the parent endoscope shaft 4 and be interchangeable with a flexible mini-endoscope of the same diameter, or with similar rigid telescopes having different angled field collecting lenses. Most importantly, the telescope system is designed to have independent movement (rotation and advance/withdrawal) within the parent endoscope. The optical system can then be moved independently and in unison with the instruments as desired. This arrangement overcomes the problems of the so-called inverse square law, according to which the distortion of objects as viewed through the optical telescope increase dramatically as their distance from the end of the telescope decreases. The off-centre viewing lens 14 is attached to a CCD camera 15, or alternatively (not shown) this lens forms part of an integral CCD camera system.

The rigid endoscope ideally has a shaft 4 of about 15 cm in length, and the telescope 2 is able to extend a further approximately 30 mm beyond the end of the endoscope. The shafts of the instruments (to be described below) need therefore to be generally about 25 cm in length.

A modification of the illustrated system will now be mentioned by way of example. In the modification (not shown), a flexible endoscope system is used in place of the rigid system described above. The flexible system can be used in conjunction with the rigid shaft 4 (as in the case of the mini-endoscope), or separately as the main endoscopic system. A variety of sizes are possible, depending upon the number of channels employed. The ideal size is around 4 mm diameter and 15 cm length. A steerable endoscope is preferred, but in this case should include facilities for locking the endoscope in one position, so as to free the surgeon's hands to concentrate on manipulating the instrumentation. A flexible mini-endoscope would provide a useful contrary or juxtaposed view of the tissue/instrument working interface when used in conjunction with the rigid parent endoscope. It is not necessary for this system to have a working channel, irrigation or fluid escape channels. All available space could therefore be used for the optical system and preferably some additional lighting.

Returning now again to the illustrated embodiments, the congruent optical bundles of the illustrated fibre optic lighting system 3 should be positioned so as to provide an optimal view of the two working channels 5,6. This provides visualization of the entry point for the instruments into the surgical field, and an optimal view of the tissue/instrument working interface. The two working channels should be non-dedicated and carry no teats, taps or stops. Irrigation fluid is delivered across the optical bundle as described above, so as to provide a clear view at all times.

The surgical instrumentation will now be described with particular reference to FIGS. 2 to 15.

Each surgical instrument 1 generally includes proximal manually operable instrument control means 1a and distal operative means 1b coupled thereto, the operative and control means being spaced mutually apart by a shaft 21, and an ergonomic handle 16 in general proximity to the control means whereby the surgeon can hold the instrument.

The handle 16 is connected to the shaft 21 of the instrument via a two-part separable handle mounting block 22a, 22b, and is provided with surface depressions 17,18,19,20 arranged to accommodate respectively the surgeon's thumb tip, index finger tip, middle finger tip and fourth finger tip. The surgeon thus grips fast the handle directly between the thumb and middle finger. The depressions can be provided with ridged gripping surfaces, as shown in more detail in FIGS. 11(a) and 11(b).

Figure 10:
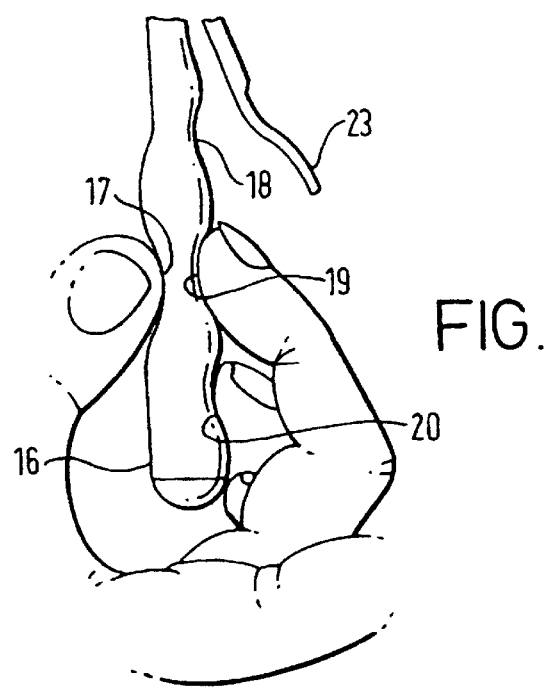
FIG. 10 shows the handle portions of the surgical instrument of FIGS. 2 to 9 in use.

Furthermore the handle, while being generally elongate, extends no more than about 5 cm beyond the point of grip and the instrument is thus adapted to permit the surgeon to move his/her hand around the handle in unrestricted movement while maintaining the grip (see, for example, FIG. 10).

The instrument control means as illustrated are mounted to the handle mounting block part 22b and comprise a trigger 23 and/or knurled wheel 24, but any analogous actuating members may alternatively (or additionally) be used. The trigger 23 and/or wheel 24 are arranged to be operable by the surgeon's index finger without releasing the grip on the handle.

The handle is mounted fast to the instrument and extends at right angles to the direction of the shaft. The handle, handle block part 22b and control means are provided as a removable, reusable, unit, which is sterilisable for reuse and constructed from lightweight materials to minimise hand fatigue.

The handle block part 22a and the shaft 21 are provided as a disposable unit, releasably attachable (e.g. by push or snap fitting) to the handle/control means unit described above.

The instrument systems are soft, light-weight and responsive and have been developed to provide accurate manoeuvrability and simultaneous targeting of any binary combination of instruments within the operative field. Despite being introduced parallel to the main axis of the endoscope the instruments are designed to reach a target point independent of the position of the endoscope within the operative field. The principal method by which this is achieved is via controlled deflection of the instrument working portion, with a radius of operation commensurate with the primary endoscopic viewing area, and in proportion to the size of the anatomical structures encountered.

All the instruments illustrated have at least a primary (distal deflection) formation, whereby the distal end of the instrument can be moved laterally to and fro within the field of view. This function is controlled by the surgeon's actuation of the trigger 23 or wheel 24 via an index finger.

Figure 2:
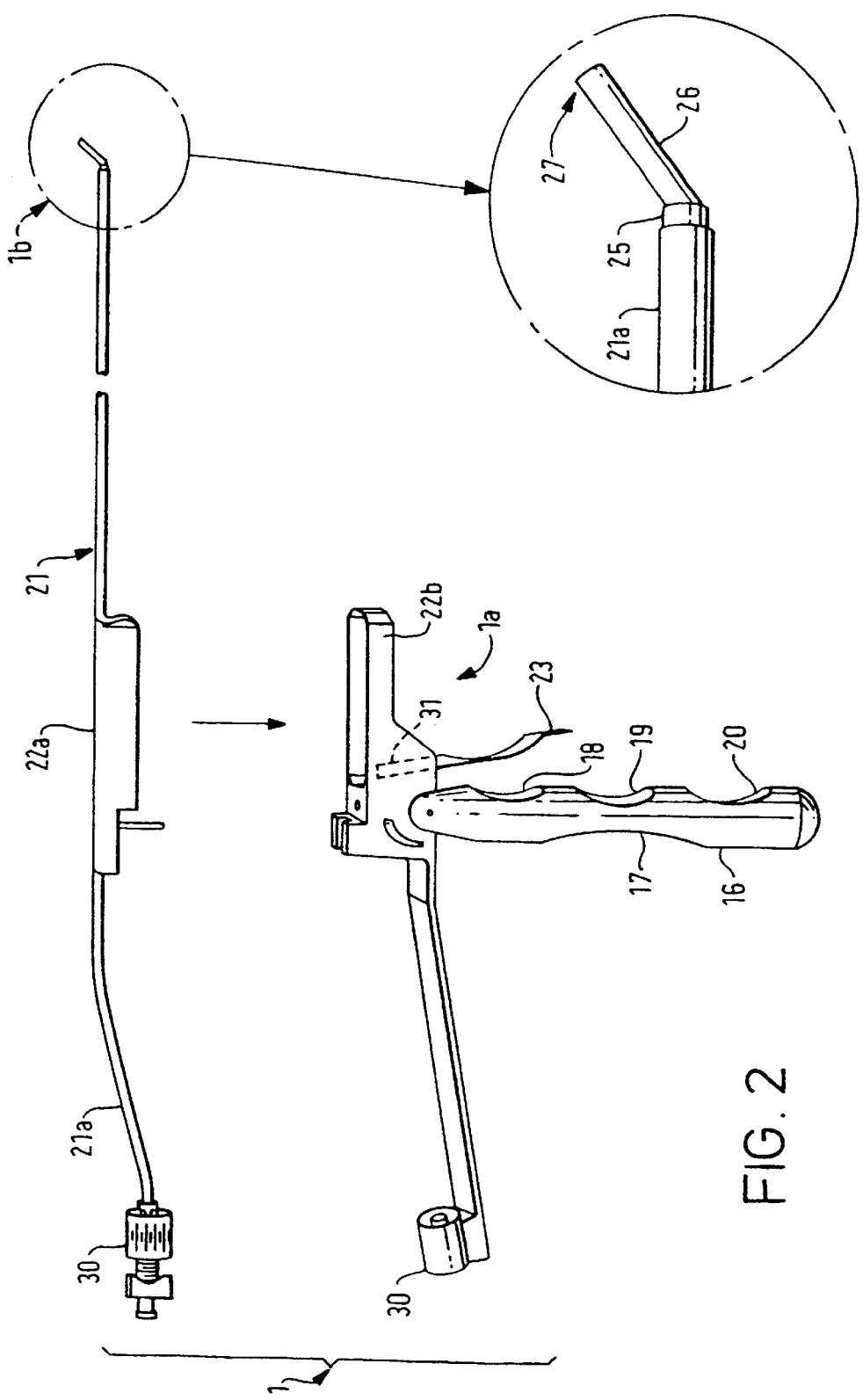
FIG. 2 shows in exploded perspective view a suction surgical instrument.
Figure 4:
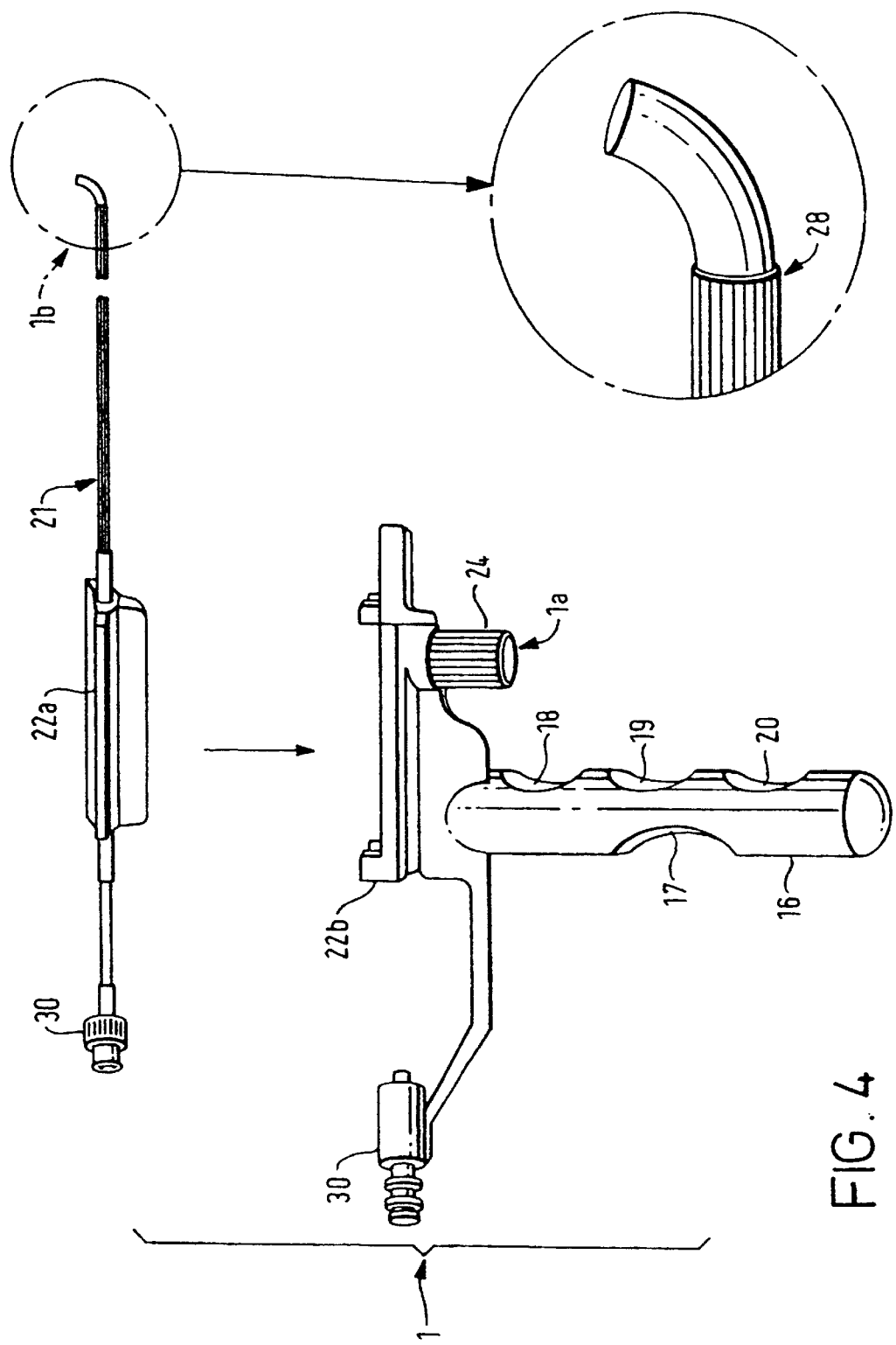
FIG. 4 shows in exploded perspective view an alternative suction surgical instrument.
Figure 5:
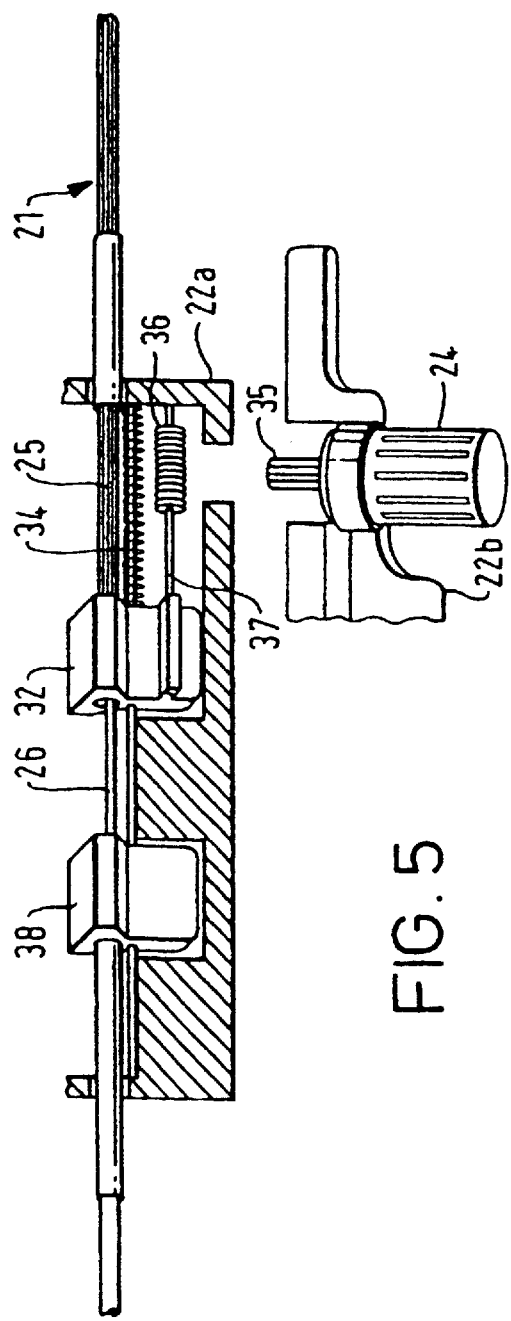
FIG. 5 shows a schematic view of the internal mechanism of the handle portion of the surgical instrument of FIG. 4.
Figure 13:
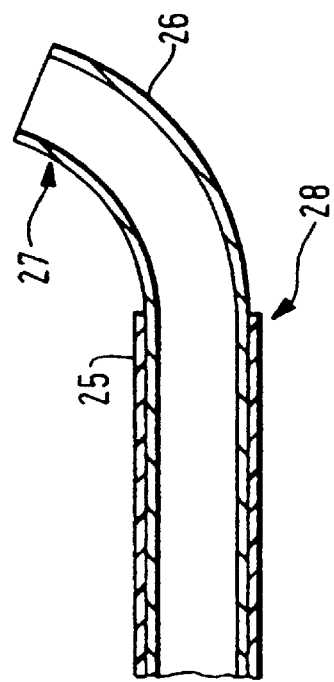
FIG. 13 shows a longitudinal sectional view of the distal end portion of the suction instrument of FIGS. 4 and 5.
Figure 6:
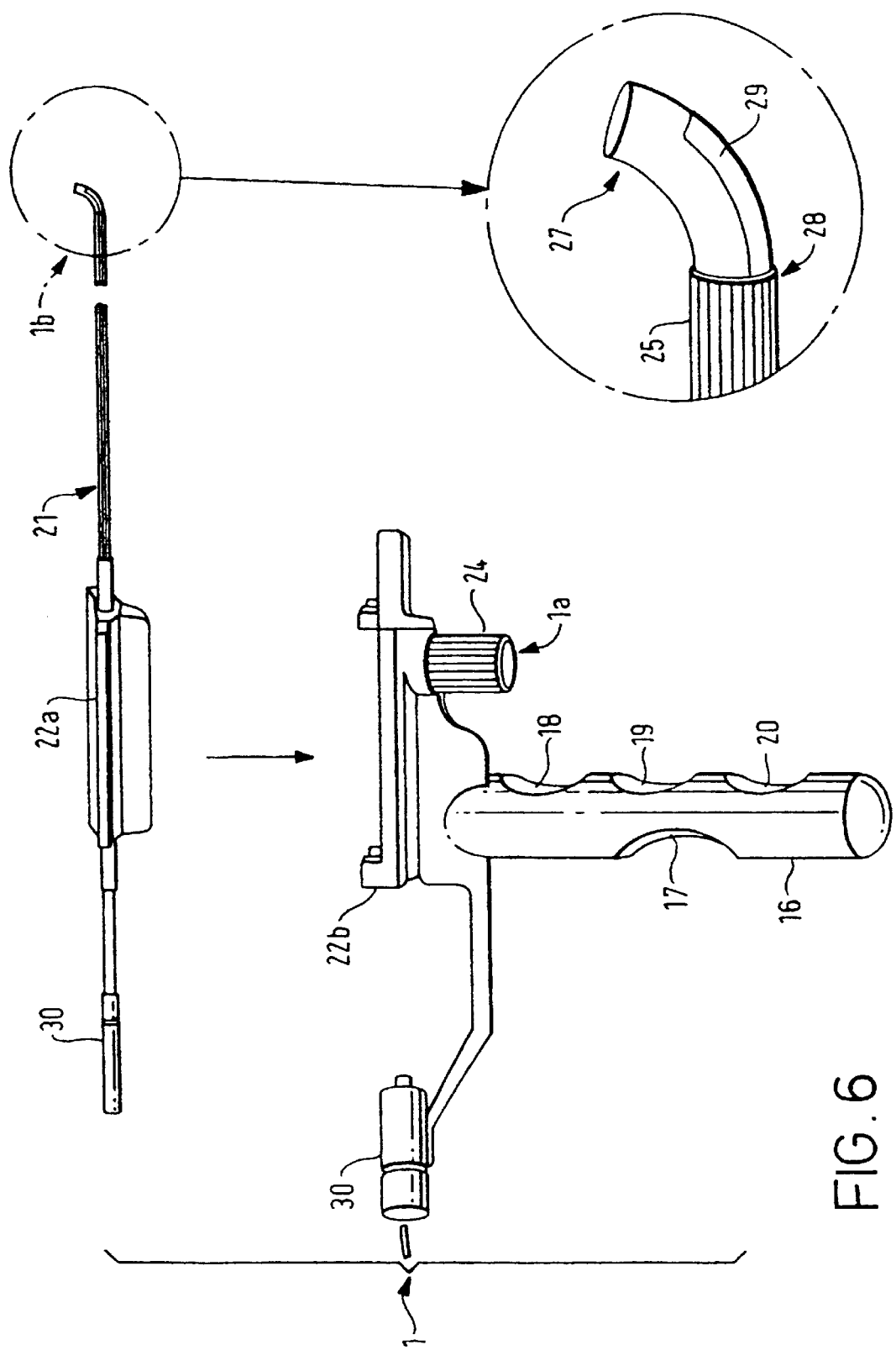
FIG. 6 shows in exploded perspective view a laser surgical instrument.
Figure 7:
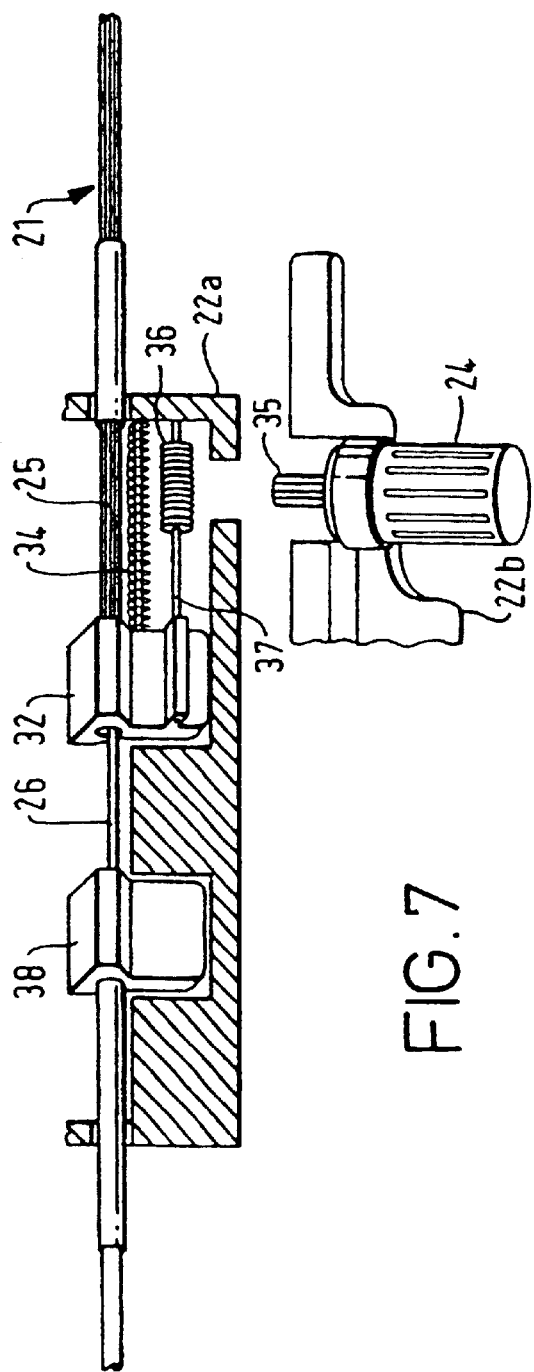
FIG. 7 shows a schematic view of the internal mechanism of the handle portion of the surgical instrument of FIG. 6.
Figure 14:
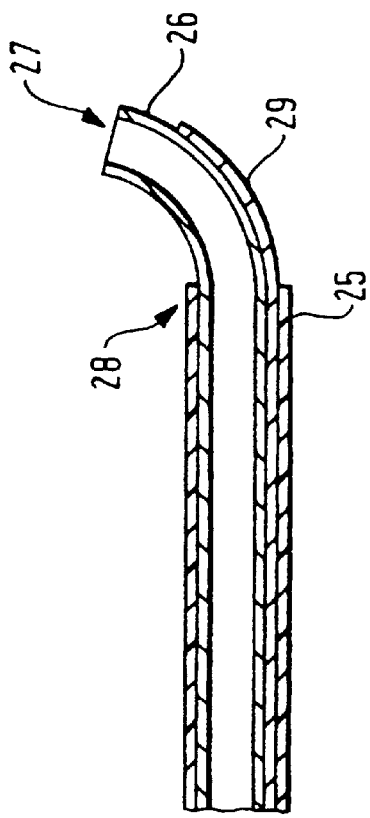
FIG. 14 shows a longitudinal sectional view of the distal end portion of the laser instrument of FIGS. 6 and 7.

In the unifunctional systems shown in FIGS. 2, 3 and 12 (a suction instrument), 4, 5 and 13 (suction instrument) and 6, 7 and 14 (a laser applicator), the operative coupling system whereby this actuation moves the distal end 1b of the instrument comprises a generally firm but pliant outer tube 25 (e.g. of plastic) constituting an outer sheath part of the shaft 21 of the instrument.

An operative inner part 26 of the shaft of the instrument in each case, namely a suction tube (FIGS. 2 to 5, 12 and 13) or a 400 $\mu$ or 600 $\mu$ laser fibre (FIGS. 6, 7 and 14), lies within the outer tube 25, and a distal end 27 thereof projects from a distal end 28 of the outer tube 25 and is angulated away from the axis of the instrument (e.g. at an angle of between about 15° and 75°, more particularly between about 30° and 60°, from the axis) at or near the point of exit from the distal end of the tube 25. Where the operative inner part of the shaft of the instrument (e.g. the laser fibre of FIGS. 6 and 7) has no inherent rigidity and cannot maintain the angulation, a firm but bendable sheath or gutter (e.g. of elastic metal) 29 may support the operative inner part of the shaft of the instrument in the desired configuration. The lateral deflection of the instrument distal end 27 is effected by relative sliding movement of the outer tube 25 and the operative inner part of the shaft of the instrument at the point of angulation.

The operative inner part 26 of the shaft of the instrument is anchored to the handle part via suitable connector pieces 30 and the outer tube 25 of the shaft is arranged to be slidingly movable over the operative inner part 26. In the case of a suction tube, for example, the connector piece 30 will be adapted to connect to the standard operating theatre suction system.

The trigger 23 of the instrument control means is pivotally mounted to the handle block part 22b so that actuation and deactuation of the trigger by the surgeon causes respectively forward and reverse movement of a lever arm 31 of the trigger within the block part 22b, as shown in more detail in FIG. 3. This lever arm protrudes into a receiving hole provided in a reciprocally slidable saddle 32 housed within the disposable part 22a of the handle block when the parts 22a and 22b are fitted together, and the lever arm 31 thereby engages in a cam-like arrangement with the reciprocally slidable saddle 32, which in turn is mounted to the outer tube 25. The saddle 32 is linked to a fixed portion 33 of the block part 22a via a compression spring 34.

On squeezing of the trigger 23 by the surgeon's finger a longitudinal sliding movement is mechanically imparted, via lever arm 31 and saddle 32, to the outer tube 25 causing the distal end 28 of the tube to overlie the angulated portion of the instrument, which thereby causes the distal end 27 of the instrument to straighten. This deflection is induced against the restoring force of the compression spring 34, so that the instrument returns to its resting condition on release of the surgeon's finger pressure.

Where the instrument control means comprises a knurled wheel 24, as shown in FIGS. 4 to 7, a somewhat different way of achieving the same effect is used. Parts which correspond to parts in FIGS. 2 and 3 are designated the same. The wheel 24 is mounted to the block part 22b and is provided with a toothed axial cog 35, housed within the block part 22b as shown in partial cut-away view in FIGS. 5 and 7. The cog 35 cooperates with a worm 36 which turns a threaded shaft 37 mating with a threaded bore in the reciprocally slidable saddle 32 housed within the disposable part 22a of the handle block. As before, the saddle 32 is mounted to the outer tube 25. The saddle 32 is thus caused to move over the operative inner part 26 of the shaft of the instrument. This operative inner part 26—namely a suction tube or laser fibre—is anchored not only via the connector pieces 30 but also via a fixed saddle 38, which is retained in the block part 22b and is secured to the suction tube or laser fibre or to a supporting sheath or gutter 29 therefor.

On turning of the knurled wheel 24 by the surgeon's finger a longitudinal sliding movement is mechanically imparted to the outer tube 25, causing the same distal deflection effect described above with reference to FIGS. 2 and 3.

The longitudinal sliding movement takes place against the restoring force of a compression spring 34, and the frictional resistance associated with the worm and threaded shaft arrangement 36,37 is selected such that when the surgeon releases his/her finger pressure on the wheel 24 the wheel is not moved under the restoring force of the spring 34, but remains in its set position. However, the compression spring 34 provides a sensitive and responsive 'touch' to the system.

If desired, the whole shaft portion of such unifunctional instrumentation may be protected within a fixed cylindrical cover tube 21a extending between the handle block part 22a and the distal point of angulation (see, for example, FIGS. 2, 3 and 12).

Figure 8:
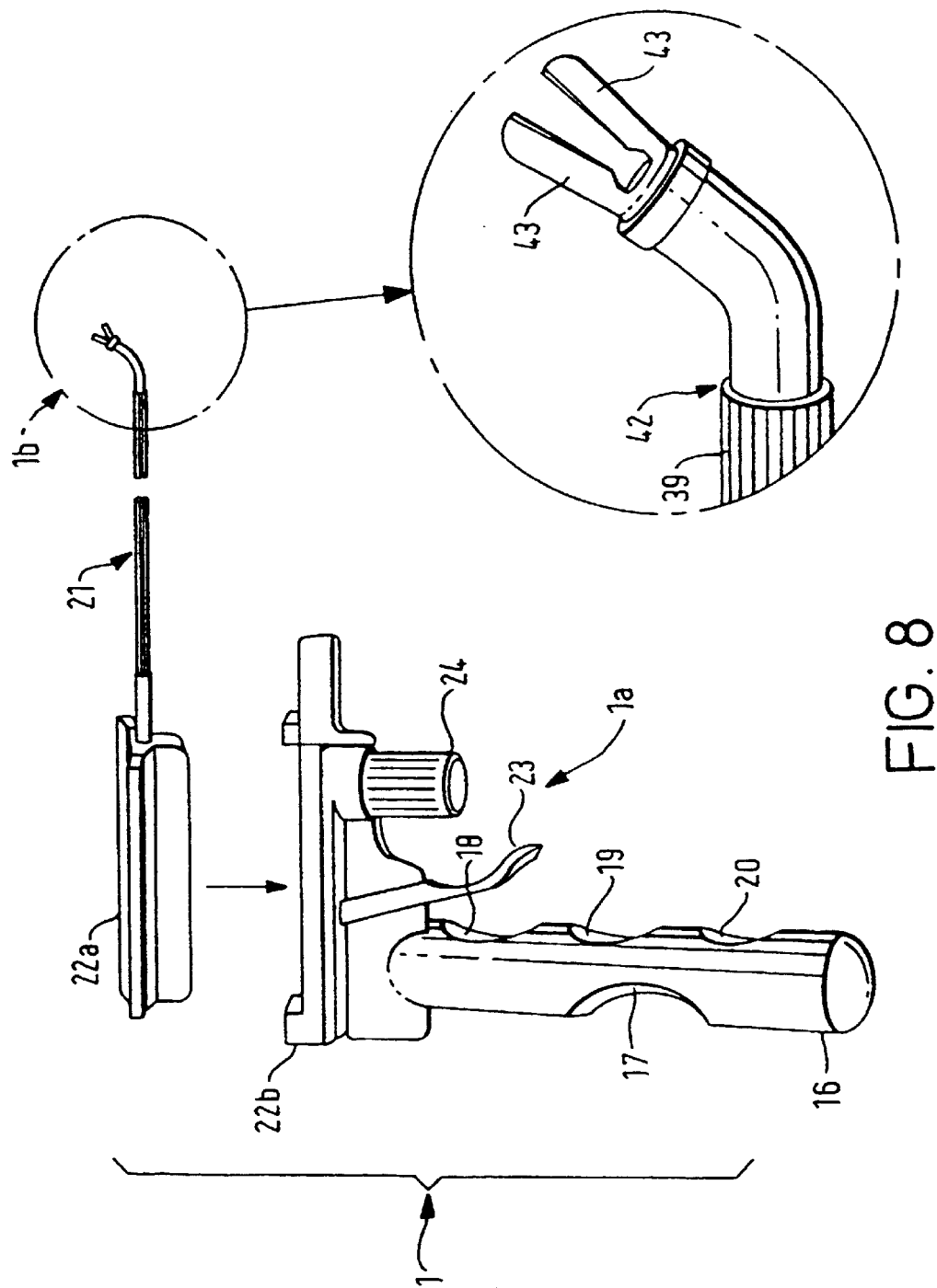
FIG. 8 shows in exploded perspective view a forceps surgical instrument.
Figure 9:
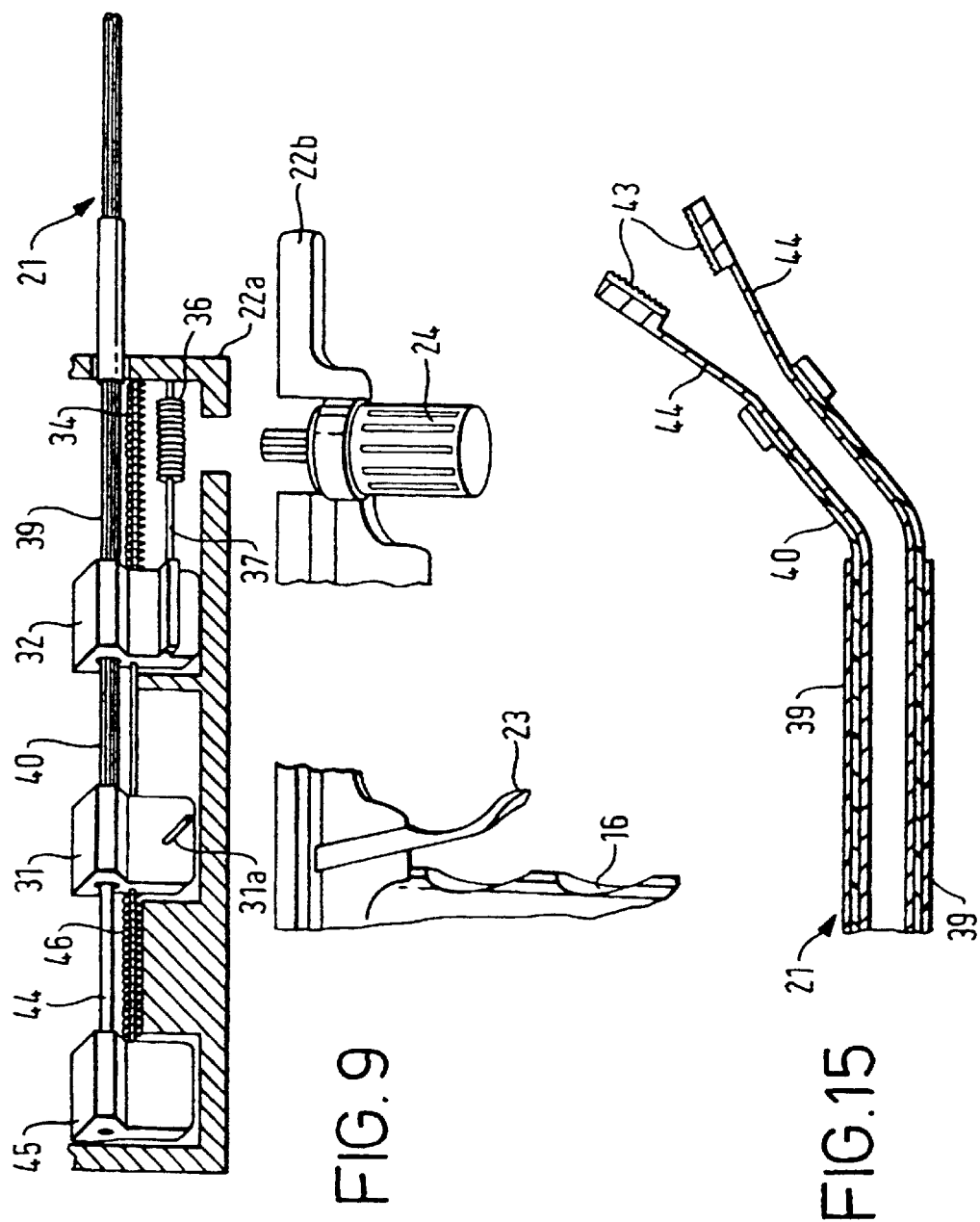
FIG. 9 shows a schematic view of the internal mechanism of the handle portion of the surgical instrument of FIG. 8.

In the multifunctional systems shown in FIGS. 8, 9 and 15, the single outer tube of the shaft is replaced by a coaxial pair of slidable tubes 39,40 constituting in effect a sheath for the shaft 21 of the instrument.

The distal end 41 of the instrument 1, namely a grasping forceps instrument as illustrated, projects away from a distal end 42 of the outer tube 39 of the pair and is angulated away from the axis of the instrument (e.g. at an angle of between about 15° and 75°, more particularly between about 30° and 60°, from the axis) at or near the point of exit of the inner tube 40 from the distal end 42 of the outer tube 39. The inner 40 and outer 39 tubes are made of firm but pliant material, such as plastic. The lateral deflection of the distal end 41 of the instrument is effected by relative sliding movement of the inner 40 and outer 39 tubes at the point of angulation.

The jaws 43 of the forceps are mounted (e.g. welded) on limbs 44 of resilient metal construction which extend from an anchor part 45 of the handle block part 22a, to which they are fixed, inside the inner tube 40, following the angulation of the inner tube as described above.

The limbs 44 project from the distal end of the inner tube 40 and splay out somewhat to end wider than the inner tube 40. Operation of the secondary instrument function, namely the opening and closing of the jaws 43 of the forceps, is achieved by independent sliding movement of the inner tube 40 over the distal end of the instrument, whereby the inner tube functions as a yoke overlying the limbs 44, which correspondingly function as control parts for the jaws 43 of the forceps. The resilience of the limbs 44 causes the jaws to close in response to sliding movement of the yoke over the splayed limbs, against the resilient restoring force of the limbs.

In a manner analogous to the unifunctional systems described above, the knurled wheel 24 of the instrument control means is coupled to the outer tube 39 via a worm 36 and threaded shaft 37 mating with a threaded bore in the reciprocally slidable saddle 32 housed within the disposable part 22a of the handle block. The wheel 24 is returned to its resting condition by the restoring force of a compression spring 34 anchored to the housing of the handle block part 22a. This causes the distal deflection function to reverse when the surgeon's finger pressure on the wheel 24 is released.

In addition, the trigger 23 of the instrument control means is coupled to the inner tube 40 via a lever arm (not shown) engaging via side pins 31a a slidable saddle 31 within the block part 22a. The saddles 31 and 32 are aligned along a common axis. The trigger 23 is returned to its resting condition by the restoring force of an expansion spring 46 anchored to the anchor part 45 of the handle block part 22a. This causes the forceps closing function to reverse when the surgeon's finger pressure on the trigger 23 is released.

The handle block part 22a is preferably supplied with the associated instrumentation already mounted thereto, as a sealed disposable unit. The handle block part 22b and associated handle is suitably formed of plastics and sealed to prevent entry of any surgical fluids into the mechanism. The handle block part 22b and associated handle is preferably reusable and is sterilised between operations by autoclaving or other conventional sterilisation method. To assemble the instrumentation for use, the surgeon merely snap-fits or clip-fits parts 22a and 22b together, as shown by the large arrows in FIGS. 2, 4, 6 and 8. At the end of the surgical procedure the parts are disassembled in the reverse way, part 22a and associated instrumentation are discarded and part 22b and the handle sterilised for reuse.

Figure 11:
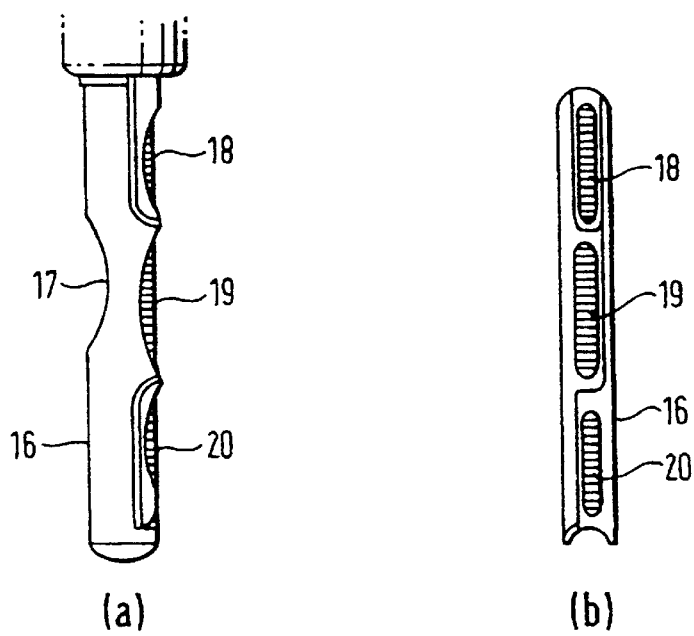
FIG. 11 shows an (a) front and (b) side views of an alternative design of handle for the surgical instruments of FIGS. 2 to 9.

The handles 16 of the instruments require specific construction, owing to the need to introduce and operate the instruments in a parallel fashion down the endoscope shaft. They are manufactured from light-weight materials to reduce hand fatigue and increase responsiveness, and the pencil shape is designed to facilitate positional changes of the hand when rotating the instrument around its long axis within the endoscope. The handle is held principally at its midpoint between the third finger and thumb which then permits unhindered rotation of the instrument around 180°. The index finger or alternatively fourth finger is then used to activate the primary, or secondary function controls, depending on the disposition of the hand. FIG. 11 shows generally how the depressions provided in the handle 16 of the instrumentation illustrated in FIGS. 2 to 9 can be ridged to provide optimum grip for the surgeon's finger tips.

Referring particularly to FIGS. 1 and 16 to 18, a novel fibre optic light guide system 3 is employed in the illustrated embodiments. This light guide 3 comprises a light-conveying optical fibre bundle 3a having a distal end for illuminating the operating zone. The distal end is provided with a convex end surface whereby the conveyed light is focused onto the operating zone.

The fibre bundle is integral with the support shaft 4 so that the distal end of the fibre or fibre bundle corresponds to the distal end of the support shaft. The convex end surface of the fibre or fibre bundle extends to overlie the distal end of the shaft. The channels 5,6,7,9,10 of the shaft are continued through the distal end portion of the light guide overlying the end of the shaft. Simple removable channel occluders (not shown) are used to temporarily close the channels and reconstitute a curved surface for the convex end surface during introduction of the assembly into the patient, to prevent tissue or fluids from fouling the channels.

The intention in developing this system was to provide, for the first time, a neurosurgical endoscopic system and instrumentation specifically designed for use in bimanual multifarious endoscopic procedures, using a range of multifunctional instruments in any binary combination as required. The current standard in neuroendoscopy is best suited to unifunctional procedures, where a single, primary instrument function is performed, under direct vision and with background irrigation. These systems lack the means for concerted interaction between instruments.

By contrast, the system described above provides for controlled manipulation and targeting of the instruments within the surgical field, together with independent adjustment of the optical viewing perspective (of the instruments or the surgical field), without altering the position of the parent endoscope within the cranium. The optical telescope, or flexible mini-endoscope, is also positioned in such a way as to provide a clear view of the instruments at their point of entry into the surgical field and these are then followed throughout their trajectory to the target area. By this means the introduction of the instruments into the surgical field can be verified as safe for any given endoscopic position, before proceeding with their use. A rigid parent endoscopic system provides an inherently stable working platform, through which to manipulate the instruments throughout their range of movement. The system likewise provides stability to the proximal portion of a flexible mini-endoscope. In some ways this makes the instruments easier to handle than in microsurgery.

Use of endoscopy in most vital organs, and certainly within the brain, requires a single entry and surgical approach. For instruments to be used in this manner it is mandatory that they are introduced parallel to the main axis of the endoscope. This presents a number of problems, both at the proximal end of the endoscope (owing to the limitation of space) and at the distal (working) end. Here, the two instruments must function with minimal effort and allow for concerted targeting towards any specific point within the surgical field.

This should be performed without the need to move the position of the parent endoscope. The problem has been at least partially overcome according to the present invention by developing instruments which are introduced parallel to the main axis of the endoscope, but can be accurately and efficiently deflected distally towards any specific point. This arrangement permits concerted bimanual operation, thereby optimizing control of the surgical field and maximizing safety.

The instruments should be compliant, lightweight and responsive to permit accurate and delicate function within the operative field. They should also function independently of the position of parent endoscope, and in conjunction with the optical telescope. Consequently, as the procedure progresses it can be performed at increasing distance from the initial position of the parent endoscope. In neurosurgery it remains critical to avoid repeated readjustment of the parent endoscope within the head. This leads to increased damage to the brain.

The overall diameter of this type of endoscopic system is not as critical as with traditional unifunctional endoscopic systems, since the possibility exists for bimanual tissue dissection, and thereby to displace tissue planes as in other modes of surgery. By attaching a small CCD video camera to the viewing lens, which is itself off-set out of the way of the central area for instrument manipulation, the surgeon may operate via a high-definition monitor and is thereby completely unhindered as regards body posture and freedom of movement.

This system provides the means for more complex neurosurgery procedures to be undertaken, but neuroendoscopy requires, like microneurosurgery before it, an appreciation of the neuroanatomy and familiarization with the operating (visual) perspective, and some of the nuances encountered, but once applied the specific advantages for minimally invasive surgery are readily felt.

The foregoing broadly describes this invention without limitation to the particular examples and embodiments illustrated. Variations and modifications as will be readily apparent to those of ordinary skill in this art are intended to be included within the scope of this invention.

What is claimed is:

1. A surgical instrument assembly for use in endoscopic surgery, the assembly comprising:
    (a) a surgical instrument having a proximal control device for manually operating the instrument coupled to a distal operative device, the operative device and the control device being spaced mutually apart by a shaft, and a handle being provided in general proximity to the control device whereby a surgeon can hold the instrument;
    (b) optical means for viewing a distal end of the instrument in an operating zone within a patient; and
    (c) support means for retaining the instrument and optical viewing means in use so as to present the distal end of the instrument for viewing in the operating zone within the patient and to present the control device externally of the patient for manipulation by the surgeon;
    characterized in that: the handle is ergonomically configured as a generally elongate handle provided with opposed surface depressions arranged along the length of the handle, to accommodate at least a thumb tip and middle finger tip of the surgeon whereby the surgeon can grip fast the handle substantially directly between thumb and middle finger;
    the handle extends no more than about 5 cm beyond said surface depressions and the instrument is adapted to permit the surgeon to use the handle to rotate the instrument about the long axis of the shaft of the instrument while simultaneously rotating his/her hand around the handle in unrestricted movement with the palm of the hand passing around the end of the handle while maintaining the grip between thumb and middle finger, and
    the proximal control device is provided in general proximity to the handle, such that the surgeon can operate the surgical instrument using his/her index finger or fourth finger without releasing the grip between thumb and middle finger.

2. A surgical instrument assembly according to claim 1, in which the handle is mounted fast to the instrument without pivotal movement between handle and instrument.

3. A surgical instrument assembly according to claim 1, in which the handle extends at right angles to the longitudinal direction of the shaft.

4. A surgical instrument assembly according to claim 3, in which the handle and control means are releasably mounted to the shaft as a removable, reusable, unit.

5. A surgical instrument assembly according to claim 1, in which the handle is hollow and is formed as a releasable pair of handle halves.

6. A surgical instrument assembly for use in endoscopic surgery, the assembly comprising:
    (a) a surgical instrument having a proximal control device for manually operating the instrument coupled to a distal operative device, the operative device and the control device being spaced mutually apart by a shaft, and a handle being provided in general proximity to the control device whereby a surgeon can hold the instrument;
    (b) optical means comprising an endoscope telescope and lighting system, for viewing a distal end of the instrument in an operating zone within a patient; and
    (c) support means for retaining the instrument and optical viewing means in use so as to present the distal end of the instrument for viewing in the operating zone within the patient and to present the control device externally of the patient for manipulation by the surgeon;

characterized in that the lighting system is independent of the endoscope telescope and is of fixed location relative to the support means to illuminate a predetermined region of the operating zone relative to the support means;

the instrument shaft is retained by the support means in an orientation generally parallel to, but offset from, the endoscope telescope;

the endoscope telescope is movable in conjunction with the surgical instrument relative to the support means and lighting system;

the handle is ergonomically configured as a generally elongate handle provided with opposed surface depressions arranged along the length of the handle, to accommodate at least a thumb tip and middle finger tip of the surgeon whereby the surgeon can grip fast the handle substantially directly between thumb and middle finger; the handle extends no more than about 5 cm beyond said surface depressions and the instrument is adapted to permit the surgeon to use the handle to rotate the instrument about the long axis of the shaft of the instrument while simultaneously rotating his/her hand around the handle in unrestricted movement with the palm of the hand passing around the end of the handle while maintaining the grip between thumb and middle finger; and the proximal control device is provided in general proximity to the handle, whereby the surgeon can operate the surgical instrument using his/her index finger or fourth finger without releasing the grip between thumb and middle finger.

7. The surgical instrument assembly of claim 6 wherein the surgical instrument part (a) is a surgical instrument having a proximal instrument control device operable by a surgeon coupled to a distal operative device, the operative device and the control device being spaced mutually apart by a shaft having proximal and distal ends, the shaft being associated with or comprising longitudinally slidable parts bearing against elastic or resilient operative portions at the distal end of the shaft and means being provided for causing longitudinal sliding of said parts in response to operation of the instrument control device to effect said operative coupling of the operation control device;

characterized in that the surgical instrument is a suction tube or laser fibre instrument and the instrument control device controls a distal deflection fuction provided by the distal operative device, the slidable parts comprise an outer part of the shaft of the surgical instrument and an inner part of the shaft of the surgical instrument lying within the outer part, and the distal end of the inner part of the shaft projects from a distal end of the outer part and is angulated away from the axis of the surgical instrument at or near the point of exit from the distal end of the outer part; or, characterized in that the surgical instrument has closable and openable jaws, blades or cusps and the instrument control device controls said closing and opening as well as a distal deflection function provided by the distal operative device, the slidable parts comprise a coaxial pair of first and second slidable tubes the first housed within the second, together comprising an outer part of the shaft of the surgical instrument, and an inner part of the shaft of the surgical instrument lying within the outer part, the distal end of the first tube of the outer part of the shaft projects from the distal end of the second tube of the outer part and is angulated away from the axis of the surgical instrument at or near the point of exit from the distal end of the outer part, and the inner part of the shaft of the surgical instrument, lying within the said tube pair, comprises control parts for the jaws, blades or cusps, which project from the distal end of the first tube of the outer part.

8. The surgical instrument assembly of claim 6 or 7, wherein the lighting system comprises a fibre optic light guide for illuminating an operating zone, wherein the fibre optic light guide comprises elongate light-conveying optic fibres or fibre bundles having a distal end for illuminating the operating zone and contiguous at their distal end with a distinct, smooth, protective and physiologically benign, transparent, refractive lens providing a convex end surface, whereby the conveyed light is focused onto the operating zone and the optic fibres are not injured or fouled by tissue, debris or blood from the patient.

9. A surgical instrument assembly according to claim 6, in which the handle is mounted fast to the instrument without pivotal movement between handle and instrument.

10. A surgical instrument assembly according to claim 2 or claim 6 or claim 9, in which the handle extends at right angles to the longitudinal direction of the shaft.

11. A surgical instrument assembly according to claim 10, in which the handle and control device are releasably mounted to the shaft as a removable, reusable, unit.

12. A surgical instrument assembly according to claim 6, in which the handle is hollow and is formed as a releasable pair of handle halves.

13. A surgical instrument assembly according to claim 1 or claim 6, in which the instrument is adapted to permit the surgeon to use the handle to rotate the instrument through 180° of rotation about the long axis of the shaft of the instrument while maintaining the grip between thumb and middle finger at approximately the midpoint along the length of the handle.

14. A surgical instrument assembly according to claim 1 or claim 6, wherein the opposed surface depressions are located at approximately the midpoint along the length of the handle.

15. A surgical instrument assembly according to claim 1 or claim 6, wherein the proximal control device is selected from the group consisting of triggers, levers, wheels and any combination thereof, operatively coupled to the distal operative device of the instrument.

16. A surgical instrument assembly according to claim 1 or claim 6, wherein the surgical instrument is selected from the group consisting of suction instruments, dissection forceps, laser fiber applicators, non-crushing grasping forceps, biopsy rongeurs, scissors, arachnoid dissectors and bipolar diathermy instruments.

* * * * *